(12) United States Patent
Cox et al.

(10) Patent No.: US 10,751,018 B2
(45) Date of Patent: Aug. 25, 2020

(54) MULTIPLE-APERTURE COMPUTERIZED TOMOGRAPHY SYSTEMS

(71) Applicant: PRINCIPLE IMAGING CORPORATION, West Yellowstone, MT (US)

(72) Inventors: John D. Cox, Gainesville, FL (US); Gary R. Cantu, West Yellowstone, MT (US); Iain Hueton, Ogden, UT (US)

(73) Assignee: PRINCIPLE IMAGING CORPORATION, West Yellowstone, MT (US)

( * ) Notice: Subject to any disclaimer, the term of this patent is extended or adjusted under 35 U.S.C. 154(b) by 328 days.

(21) Appl. No.: 15/841,812

(22) Filed: Dec. 14, 2017

(65) Prior Publication Data

US 2018/0289348 A1 Oct. 11, 2018

(51) Int. Cl.
| | | |
|---|---|---|
| *A61B 6/03* | (2006.01) |
| *A61B 6/00* | (2006.01) |
| *A61D 3/00* | (2006.01) |
| *A61B 6/02* | (2006.01) |
| *A61B 6/04* | (2006.01) |

(52) U.S. Cl.
CPC .............. *A61B 6/508* (2013.01); *A61B 6/025* (2013.01); *A61B 6/032* (2013.01); *A61B 6/035* (2013.01); *A61B 6/04* (2013.01); *A61B 6/4007* (2013.01); *A61B 6/4078* (2013.01); *A61B 6/4085* (2013.01); *A61B 6/4452* (2013.01); *A61B 6/486* (2013.01); *A61B 6/5241* (2013.01); *A61D 3/00* (2013.01); *A61D 2003/006* (2013.01)

(58) Field of Classification Search
None
See application file for complete search history.

(56) References Cited

U.S. PATENT DOCUMENTS

| | | | | |
|---|---|---|---|---|
| 7,103,137 | B2 * | 9/2006 | Seppi ..................... | G01N 23/04 378/57 |
| 7,369,640 | B2 * | 5/2008 | Seppi ..................... | G01N 23/04 378/57 |
| 7,388,941 | B2 | 6/2008 | Sukovic et al. | |
| 7,672,422 | B2 * | 3/2010 | Seppi ..................... | G01N 23/04 378/114 |

(Continued)

OTHER PUBLICATIONS

Varex 4030CB Cone Beam X-Ray Detector, Varex Imaging, 2017, 2 pages.

(Continued)

*Primary Examiner* — Thomas R Artman
(74) *Attorney, Agent, or Firm* — Rimon Law

(57) ABSTRACT

A scanning system having a plurality of X-ray sources together with a single X-ray detector that uses sequentially emitted overlapping fan-shaped or cone-shaped beams to image a target such as the leg of a horse. The X-ray detector is rotated closer to the target and the X-ray emitter sources are rotated at a greater distance from the target. The positioning systems of the X-ray detector and the X-ray sources may be operated independently of one another, with each of the X-ray detector and the X-ray sources being also rotated about separate axes passing therethrough (while they are both being rotated around the target) as a way to keep the X-ray sources and the X-ray detector parallel to one another while working in very tight spaces.

31 Claims, 18 Drawing Sheets

(56) References Cited

U.S. PATENT DOCUMENTS

| | | | | |
|---|---|---|---|---|
| 8,509,387 B2* | 8/2013 | Tsujii | ............. | A61B 6/06 378/122 |
| 8,537,965 B2* | 9/2013 | Dafni | ............. | A61B 6/032 378/4 |
| 8,605,854 B2* | 12/2013 | Hoernig | ............. | A61B 6/025 378/37 |
| 8,995,610 B2* | 3/2015 | Ying | ............. | A61B 6/032 378/9 |
| 9,245,659 B2* | 1/2016 | Tsujii | ............. | A61B 6/06 |
| 9,277,899 B2 | 3/2016 | Yorkston et al. | | |
| 9,339,243 B2* | 5/2016 | Zhang | ............. | A61B 6/025 |
| 9,739,724 B2* | 8/2017 | Ying | ............. | A61B 6/032 |
| 9,934,932 B2* | 4/2018 | Mackie | ............. | A61B 6/035 |
| 10,136,870 B2* | 11/2018 | Ray | ............. | A61B 6/508 |
| 2004/0017888 A1* | 1/2004 | Seppi | ............. | G01N 23/04 378/57 |
| 2006/0285633 A1* | 12/2006 | Sukovic | ............. | A61B 6/032 378/9 |
| 2007/0003003 A1* | 1/2007 | Seppi | ............. | G01N 23/04 378/9 |
| 2008/0205583 A1* | 8/2008 | Seppi | ............. | G01N 23/04 378/9 |
| 2011/0080992 A1* | 4/2011 | Dafni | ............. | A61B 6/032 378/9 |
| 2011/0211666 A1* | 9/2011 | Ying | ............. | A61B 6/032 378/9 |
| 2011/0216884 A1* | 9/2011 | Tsujii | ............. | A61B 6/06 378/62 |
| 2012/0008739 A1* | 1/2012 | Hoernig | ............. | A61B 6/025 378/37 |
| 2013/0294582 A1* | 11/2013 | Tsujii | ............. | A61B 6/06 378/150 |
| 2014/0247919 A1* | 9/2014 | Zhang | ............. | A61B 6/025 378/62 |
| 2015/0177165 A1* | 6/2015 | Ying | ............. | A61B 6/032 378/9 |
| 2016/0361036 A1* | 12/2016 | Ray | ............. | A61B 6/508 |
| 2018/0289348 A1* | 10/2018 | Cox | ............. | A61B 6/508 |
| 2018/0353145 A1* | 12/2018 | Simon | ............. | A61B 6/107 |

OTHER PUBLICATIONS

Toshiba Intraoral Dental X-Ray Tube, Toshiba Electron Tubes & Devices Co. Ltd., date unknown, 6 pages.

* cited by examiner

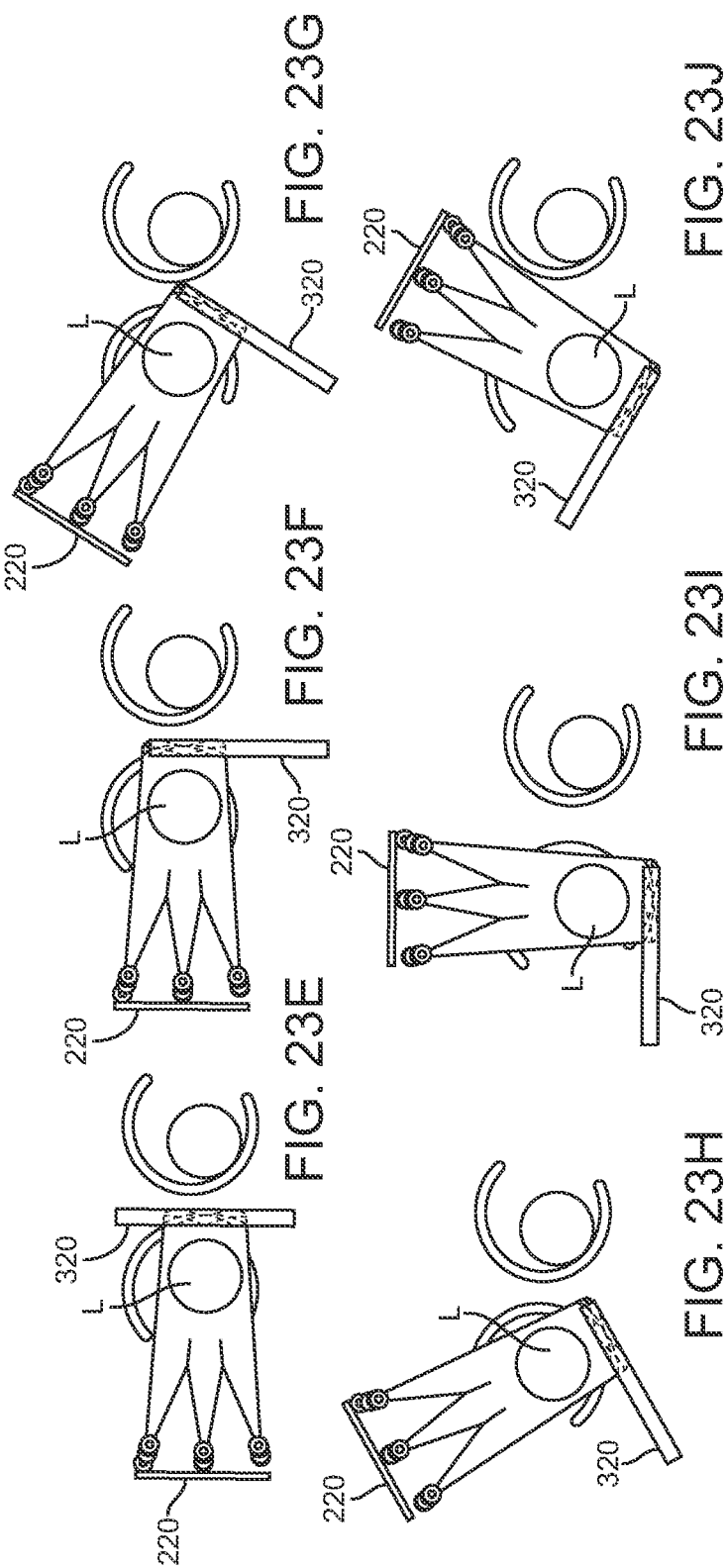

MULTIPLE-APERTURE COMPUTERIZED TOMOGRAPHY SYSTEMS

RELATED APPLICATIONS

The present application claims priority to U.S. Provisional Patent Application Ser. No. 62/434,147, entitled A Multi-Aperture Computed Tomography System, filed Dec. 14, 2016; U.S. Provisional Patent Application Ser. No. 62/445,539, entitled Equine Extremity X-ray Scanner, filed Jan. 12, 2017; and U.S. Provisional Patent Application Ser. No. 62/544,324, entitled Multi-Aperture Cone Beam CT System, filed Aug. 11, 2017, the entire disclosures of which are incorporated herein by reference in their entireties for all purposes.

TECHNICAL FIELD

The present application relates to multi-aperture scanning systems using overlapping cone-shaped computerized tomography (CT) scanning systems and fan-shaped beams for performing panoramic scanning.

BACKGROUND OF THE INVENTION

Performing CT scans of body extremities such as arms, hands, legs and feet presents special difficulties. This is especially true in the veterinary context where the patient is a horse. Specifically, it has proven especially difficult to perform good CT scans of a horse's leg for a number of different reasons, including at least the following.

First, the geometry of a standing horse is extremely difficult to work with. Specifically, the separation distance between a standing horse's legs can be as little as 4 inches apart. In addition, the image of the leg and foot should be taken under natural loading during a natural standing pose. This provides little room for a veterinarian to safely maneuver X-ray equipment around the horse's legs. In addition, a typical exam for a performance horse can require 52 separate projection images taken for each of the 4 legs. Performing such an exam quickly is very difficult.

Second, traditional CT systems use only one X-ray source and a flat panel detector and must therefore acquire image data over multiple rotations to cover the entire volume of the leg or other object being imaged. Unfortunately, the X-ray source-to-detector distance must be increased to minimize the number of rotations required. This is difficult to achieve in tight geometries. Moreover, to fully illuminate the height of the detector, a significant source-to-image distance is required so that a standard cone-beam X-ray beam can expand enough to cover the rotating detector. Once again, it is difficult to work within such geometric constraints. It can also be unsafe both for the veterinarian and for the horse.

Third, despite taking a large number of images, important pathology such as stress fractures and micro-fractures can still be missed in a CT scan. To visualize such fractures, it is necessary to acquire the image with the source and detector lined up such that the crack or fracture in the bone is seen along its axis (i.e.: by lining up the seam of the crack with the X-ray beam).

Fourth, in conventional CT systems, the object to be imaged is typically placed equidistant between the source and the detector, and the source and detector are rotated around the object. This geometry is simply not possible to use with a standing horse's legs.

In short, traditional CT scanners that image whole-bodies are expensive to own and operate (especially if they image whole-bodies), and their geometries and rotational paths are completely unsuited to work with long narrow objects that are positioned close together (for example, the legs of a standing horse). Recently developed cone-beams systems have the advantage of acquiring images quickly with less expensive imaging components but have the disadvantage of being very large due to the need to rotate a flat-panel detector. Moreover, since the cone-shaped beam of the X-ray expands outwards towards the detector, the proximal side of the object being imaged will have a smaller region of exposure than the distal side. Lastly, requiring multiple rotations of the equipment increases the time to acquire the full image.

What is instead therefore desired is a system that would rapidly image a horse's leg (or any other object) in a fast period of time and within a small area of working space. As will be explained below, the present system provides solutions to these problems.

SUMMARY OF THE INVENTION

The present system provides CT scanning systems that can be used to rapidly image an elongated object such as a body extremity while working in tight geometries. In various aspects, a plurality of X-ray sources are used together with a single X-ray detector. Embodiments using both overlapping fan-shaped beams and overlapping cone-shaped beams are both contemplated, all keeping within the scope of the present system. Since the multiple X-ray beams overlap one another on the detector, the various X-ray sources are therefore preferably timed to fire sequentially.

As will be explained, separate positioning systems can be used for each of the X-ray detectors and the plurality of X-ray sources (which are preferably moved together as a unit). The advantage of such separate positioning/movement is that the panel of X-ray sources and the X-ray detector can be rotated or translated laterally to be kept parallel to face one another as the detector is moved between the horse's legs (which are positioned very close together). This can be achieved by rotating each of the X-ray source emitters and the X-ray detector about their own central vertical axes (at the same time that both the X-ray sources and the X-ray detector are also being rotated around the horse's leg).

In preferred aspects, the X-ray sources and the X-ray detector are rotated around the leg with the detector being positioned closer to the leg and the X-ray sources being positioned much farther from the leg. Thus, the X-ray detector preferably rotates around the leg or extremity with a much smaller radius, while the X-ray sources rotate around the extremity with a much larger radius. (In contrast, prior art systems place the target mid-way between the source beam emitter and the detector, with the emitter and detector connected together with a traditional C-arm).

In one preferred aspect, the present system provides a scanning system, comprising: a plurality of X-ray sources; an X-ray detector; a positioning system for rotating the X-ray detector in a first radius around the target; and a positioning system for rotating the plurality of X-ray sources in a second radius around the target; wherein the first radius is smaller than the second radius.

Optionally, the positioning systems for the X-ray detector and the X-ray sources can be connected together to simultaneously rotate the X-ray detector and the plurality of X-ray sources around the target. However, in other embodiments, the positioning systems for rotating the X-ray detector and the X-ray sources are not connected together such that the X-ray detector and the plurality of X-ray sources can be moved independently of one another.

In preferred aspects, the present system provides a control system for sequentially activating the X-ray sources. Optionally, the control system may activate different X-ray sources at the same time, but will not activate adjacent X-ray sources at the same time (i.e.: overlapping beams will not be activated at the same time).

Optionally, a longitudinal positioning system can also be used to simultaneously move the X-ray sources and the X-ray detector up and down along the length of the horse's leg (or along the length of some other long object being imaged).

In various optional aspects, the plurality of X-ray sources may either be mounted in a planar array, or mounted so as to be positioned in a spherical or cylindrical orientation with respect to the X-ray detector. In such aspects, the cone-shaped beams may even fully overlap with one another on the X-ray detector (and be fired sequentially).

The present system also includes a preferred method of scanning a target, comprising: providing a plurality of X-ray sources on a first support; providing an X-ray detector on a second support; and imaging a target by rotating the plurality of X-ray sources and the X-ray detector around the target, while sequentially emitting overlapping beams from the plurality of X-ray sources onto the X-ray detector. Using this method, the X-ray detector is preferably rotated in a smaller radius around the target than the plurality of X-ray sources are rotated around the target. Also using this method, the X-ray detector and the plurality of X-ray sources can optionally be moved independently of one another around the target.

In a first embodiment, the X-ray detector is a linear detector, and the X-ray sources are a line of emitters each emitting a fan-shaped beam. One advantage of a linear scanner is that it is much smaller than a traditional comparable flat-panel detector. This both reduces the diameter of the scanner and makes it possible to create a much longer scanning length. In addition, rotating the fan-shaped beams to be aligned with the length of the linear detector is advantageous since it avoids the need for spiral-path scanning (i.e.: moving along an object while also rotating around it). Therefore, an image of the horse's leg can be acquired in a single rotation if the linear detector and X-ray source array is long enough. This embodiment produces panoramic planar images of the target.

In a second embodiment, the X-ray detector is a planar detector, and the X-ray sources are a two-dimensional array of emitters each emitting cone-shaped beams that overlap one another on the detector. Using such a two dimensional matrix or array of individual X-ray sources that are fired in sequential order advantageously reduces the need for multiple scans and/or increases the X-ray source to detector distance. This embodiment produces Cone-Beam Computed Tomography (CT) images of the target.

Overall, the present system has the advantage of rapid image acquisition. Also, by using a multi-aperture X-ray source configuration, the present system reduces the volume and area occupied by the scanning system.

BRIEF DESCRIPTION OF THE DRAWINGS

FIGS. 23A to 23J show sequential views of the separate movement of the X-ray sources and X-ray detector of the scanning system of FIG. 14 as it images the horse's right leg.

DETAILED DESCRIPTION OF THE DRAWINGS

It is to be understood that the present scanning system encompasses features presented in different figures attached hereto, and that the attached figures are only exemplary and that possible features may be combined in different aspects of the present system, all as encompassed by the attached claims.

Figure 1:
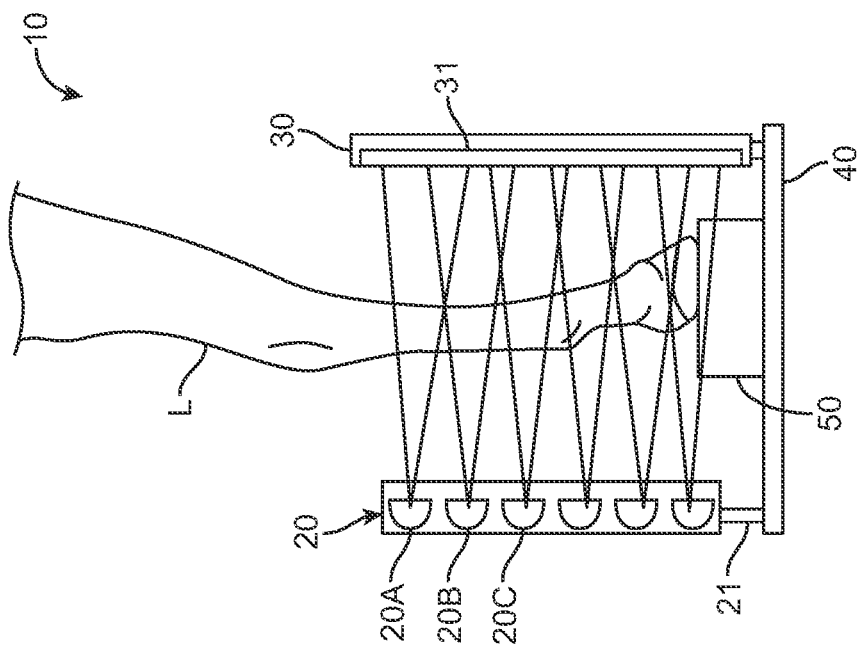
FIG. 1 is a side elevation view of a scanning system having a plurality of X-ray sources emitting overlapping fan-shaped beams directed onto a linear X-ray detector in a first position.
Figure 2:
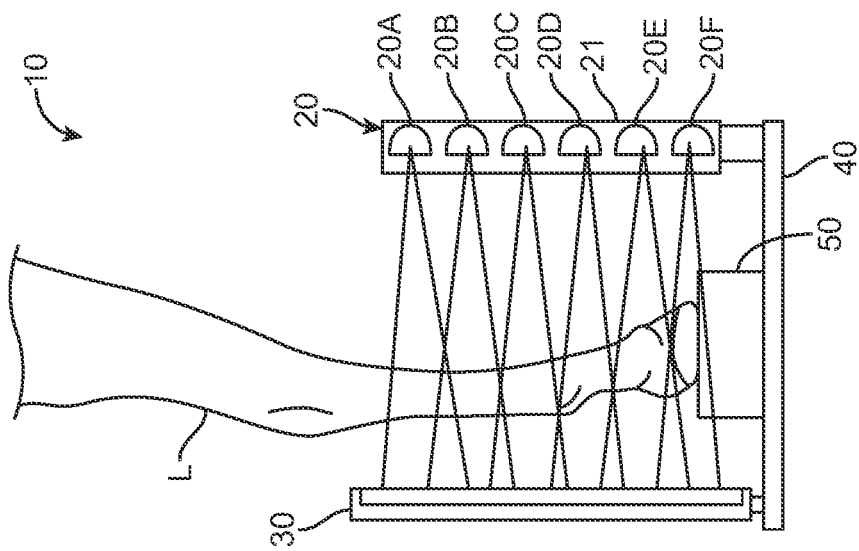
FIG. 2 is a second side elevation corresponding to FIG. 1, with the X-ray sources and detector rotated to a second position.
Figure 3:
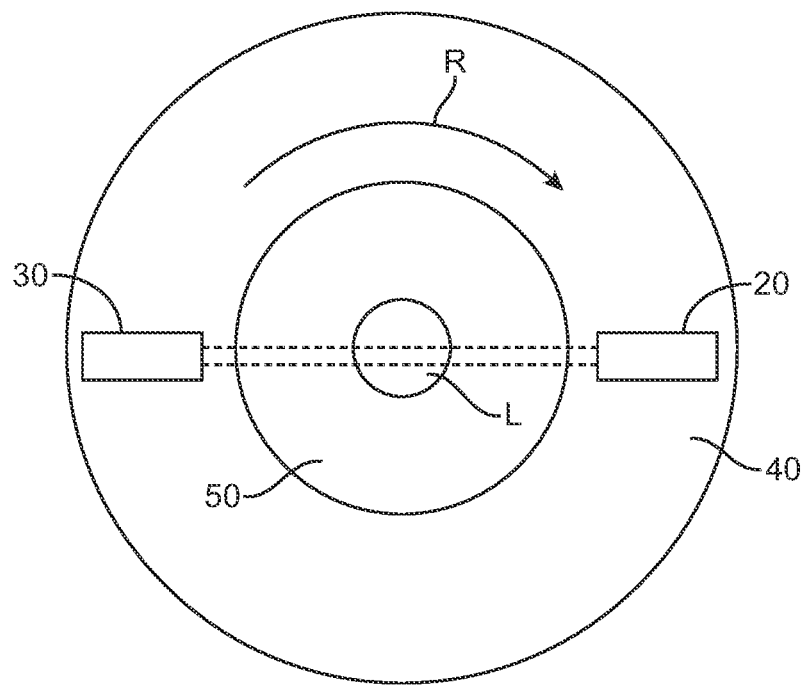
FIG. 3 is a top plan view corresponding to FIG. 1.
Figure 4:
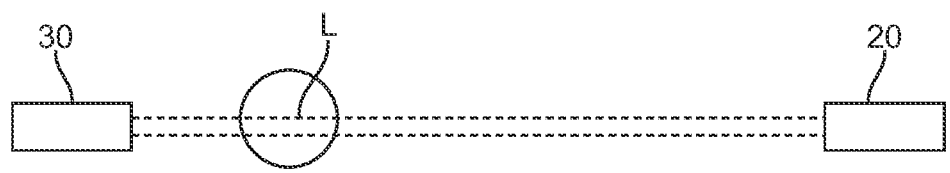
FIG. 4 is a top plan view of a plurality of X-ray sources and an X-ray detector in a preferred scanning position around an object to be scanned.
Figure 5:
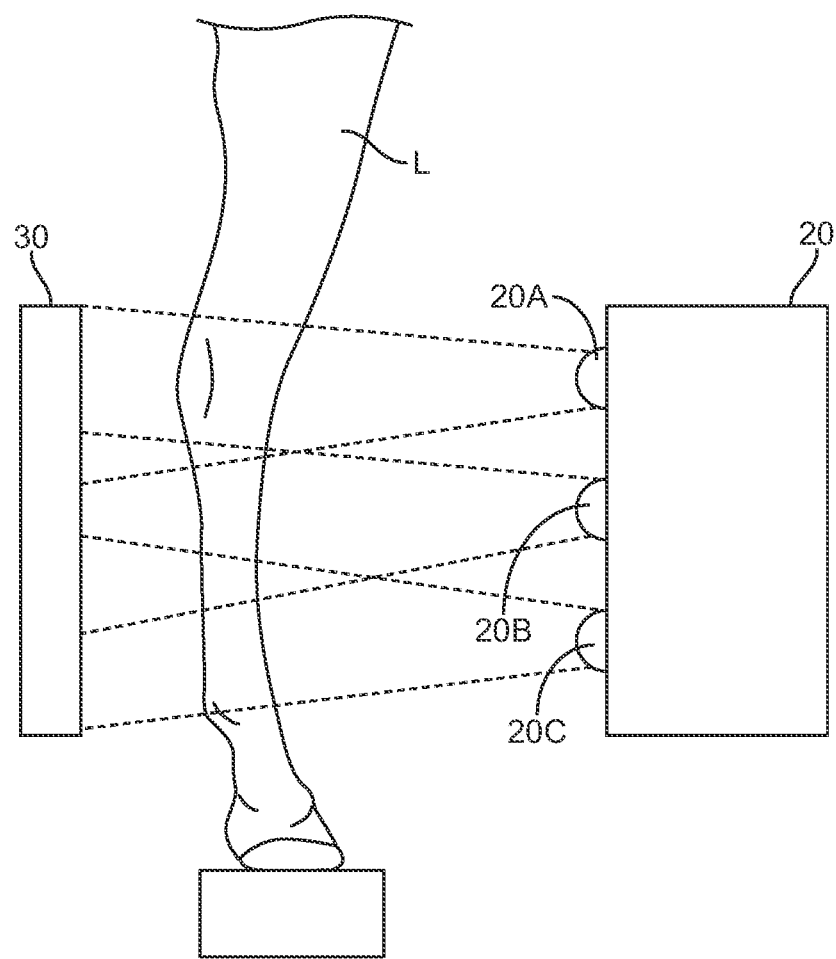
FIG. 5 is a side elevation view corresponding to the scanning system of FIG. 4.
Figure 6:
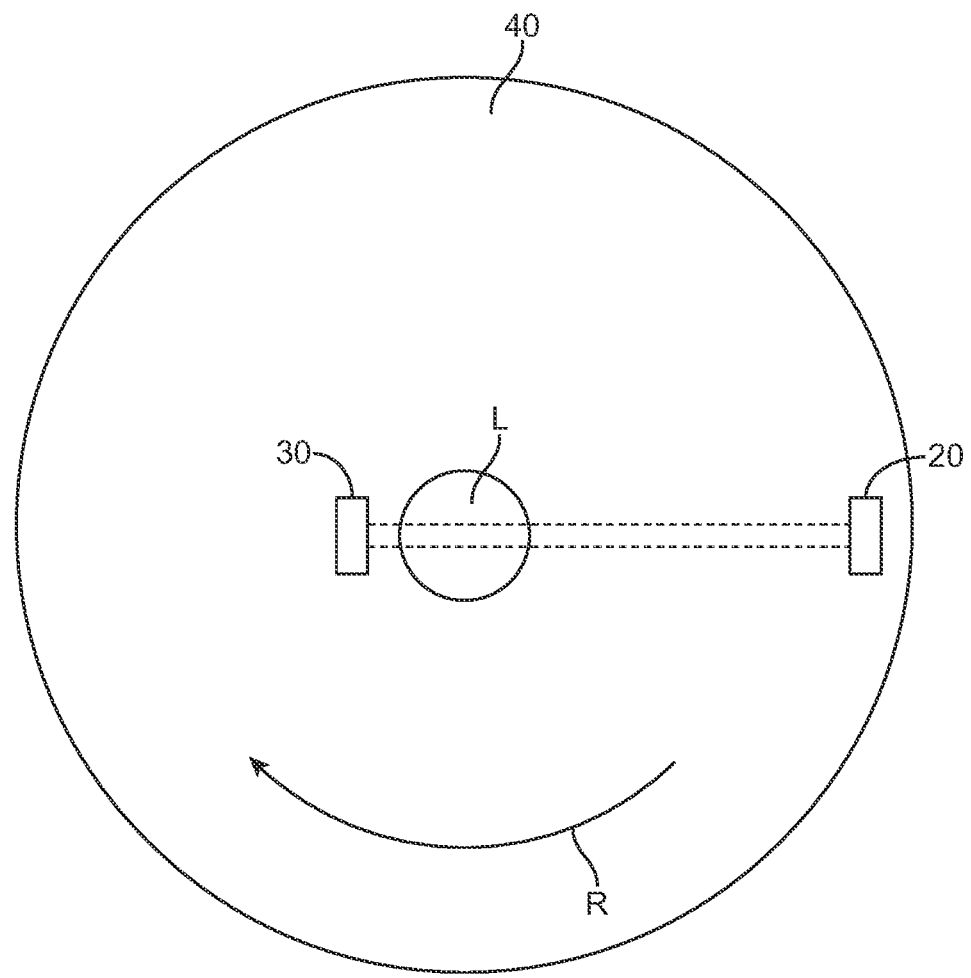
FIG. 6 is a top plan view of the scanning system of FIGS. 1 to 3, but using the preferred positioning seen in FIGS. 4 and 5.

FIGS. 1 to 3 show a first scanning system using a plurality X-ray sources that emit fan-shaped beams that are received onto a linear X-ray detector. The beams have overlapping edges. FIGS. 4 and 5 then show preferred spacing distances between the X-ray sources, the target being imaged and the linear X-ray detector. FIG. 6 shows a modified system similar to FIG. 3, but with the X-ray sources and X-ray detector re-positioned to accommodate the desired spacing of FIG. 4.

Referring first to FIGS. 1 to 3, a rotational (panoramic imaging) scanning system 10 for imaging an elongated object (such as horse's leg L) is provided. Panoramic scanning system 10 includes a plurality of X-ray sources 20 (i.e.: 20A, 20B, 20C, etc.) and a single linear X-ray detector 30. In this embodiment, X-ray sources 20 and X-ray detector 30 are both mounted onto a large rotating ring 40. As can be seen, X-ray sources 20A, 20B, 20C, etc. can all be mounted onto a single moveable support 21. As ring 40 is rotated in direction R (FIG. 3), both the X-ray sources 20 and X-ray detector 30 are rotated around leg L. Thus, in this particular embodiment, ring 40 physically connects X-ray sources 20 and X-ray detector 30 together and thus acts as the positioning system for both X-ray sources 20 and X-ray detector 30 at the same time. Specifically, X-ray sources 20 and X-ray detector 30 both rotate together around leg L as ring 40 is turned. In the center of rotating ring 40 is a circular mounting block 50 that rests on the ground to support the weight of the horse's leg. Block 50 is preferably thick enough to support the horse's hoof while raising it above the floor so that the bottom of the hoof can be imaged as well. Ring 40 can optionally have an inner diameter of 12 inches and an outer diameter of 16 inches, and preferably rotates at least 270 degrees.

Optionally, both the X-ray sources 20 and the detector 30 are each mounted to positioning ring 40 such that they will fall over or move out of the way should the horse kick or accidently bump into them (thereby preventing damage to the horse's legs). For example, X-ray sources 20 and detector 30 could be mounted onto posts 21, 31 that are held to positioning ring 40 by magnets. Such magnets would be strong enough to support the X-ray sources and the linear detector during rotation, but weak enough such that they will give way if kicked by the horse. Alternatively, both X-ray sources 30 and linear detector 30 can be tethered such that cannot become flying objects should the horse accidently kick them.

In this panoramic imaging embodiment, the X-ray sources 20 are stacked one on top of another with their fan-shaped beams overlapping along the linear detector. As also seen, X-ray sources 20 can be mounted to a single support 21 that contains the necessary electrical feedthroughs and shielding, and provides mechanical support. An exemplary X-ray source emitter 20 can be a Toshiba D-0183S, made for intraoral dental applications. These Toshiba X-ray sources are 38 mm in diameter and 72 mm in length, and produce an X-ray beam with a maximum energy of 80 kV and 15 mA for 2 seconds. An exemplary linear X-ray detector 30 can be an X-Scan XB90808, manufactured by X-Scan of San Jose, Calif. This detector has a pixel size ranging from 0.2 mm, 0.4 mm, 0.8 mm or 1.6 mm. In optional aspects, it can be coated with a scintillating phosphor such as Gadolinium Oxysulfide, Cesium Iodide and Cadmium Tungstate to absorb X-rays and produce visible light that is detected by the sensors on detector 30.

A high-voltage power supply can be used to provide electrical power to X-ray sources 20 and linear X-ray detector 30. A computer operating console (not shown) can be used to manipulate and display the acquired images. The computer control system will also have patient registration, archiving and networking connectivity.

In various aspects, image detector 30 may have multiple columns of pixels and the columns of pixels can be summed together or read out individually after each exposure cycle. The image detector in this embodiment is known as a Time-Delay-Integration (TDI) camera. For example, the scanner can be rotated to advance a distance equal to one pixel or advanced a distance of several pixels to produce overlapping views.

As can be seen in FIGS. 1 and 2, the fan-shaped X-ray beams from the adjacent X-ray sources 20 will have edges that overlap one another on the face of linear detector 30. Therefore, to acquire an image, the X-ray sources may be rapidly fired in sequence (e.g.: 20A, then 20B, then 20C, etc.). This sequential firing will be carried out as ring 40 is rotated and sources 20 and detector 30 are thereby rotated around horse's leg L.

Unfortunately, it is not desirable to place X-ray sources 20 and X-ray detector 30 equidistantly around a horse's leg for at least the following reason. Doing so would increase the diameter of the circle of rotation of the X-ray source and detector, thereby increasing the distance and/or time to acquire the images. Instead, as illustrated in FIGS. 4 and 5, it is instead desirable to place X-ray detector 30 much closer to leg L and X-ray sources 20 farther away from leg L as both are rotated around leg L. This achieves the following advantages: it allows the detector 30 to pass between the horse's legs to avoid having to image both legs at the same time (during the rotation), and it reduces the distance that the X-ray sources 20 have to rotate.

As seen in FIG. 5, the individual X-ray sources 20 are preferably positioned at a distance from one another such that their fan-shaped beams overlap on the linear detector. (Note: FIG. 5 is simplified to show only three overlapping Fan-shaped beams from three sources 20A, 20B and 20C, and the actual separation distance between the X-ray sources 20 will be determined by the emission cone angle of the X-ray source (which can be approximately 16 degrees in the case of a Toshiba D-0183S X-ray emitter)).

Since the fan-shaped beams will overlap on the linear detector, the X-ray sources 20A, 20B and 20C will be activated sequentially in rapid fire one after another. In preferred aspects, the X-ray sources are fired sequentially at a rate of 30 frames/second. It is to be understood, however, that in optional aspects, every third (or other) source produces a non-overlapping beam, therefore these third (or other) sources could instead be activated at the same time. This would have the advantage of increasing the speed of image acquisition. For example, sources 20A, 20C and 20E (see FIG. 1) could be activated simultaneously, followed by sources 20B, 20D and 20F. This particular example would have the effect of only requiring two firings of the X-ray sources 20. Therefore, it is to be understood that depending upon the width of the fan-shaped beams on detector 30, different combinations of X-ray sources can be fired at different times. In one approach, sources, 20A, 20B, 20C, etc. are each filed individually in sequence. However, should the beams be sufficiently narrow, then different combinations of sources 20 can be fired. However, adjacent sources (e.g.: 20A and 20B) would not be filed at the same time as these would overlap.

FIG. 6 illustrates a system similar to FIGS. 1 to 3, but using the preferred spacings of FIG. 4. (i.e. X-ray detector 30 is mounted closer to the center of ring 40 than X-ray sources 20). An advantage of the system of FIG. 6 is that a single positioning system (ring 40) can be used to rotate both X-ray sources 20 and X-ray detector 30 around the target object being scanned, while rotating X-ray sources 20 and X-ray detector 30 in different radii. Unfortunately, this setup is still not well suited to scan a horse's leg since the horse's left and right legs may have a clearance of as little as 4 inches therebetween.

Figure 7:
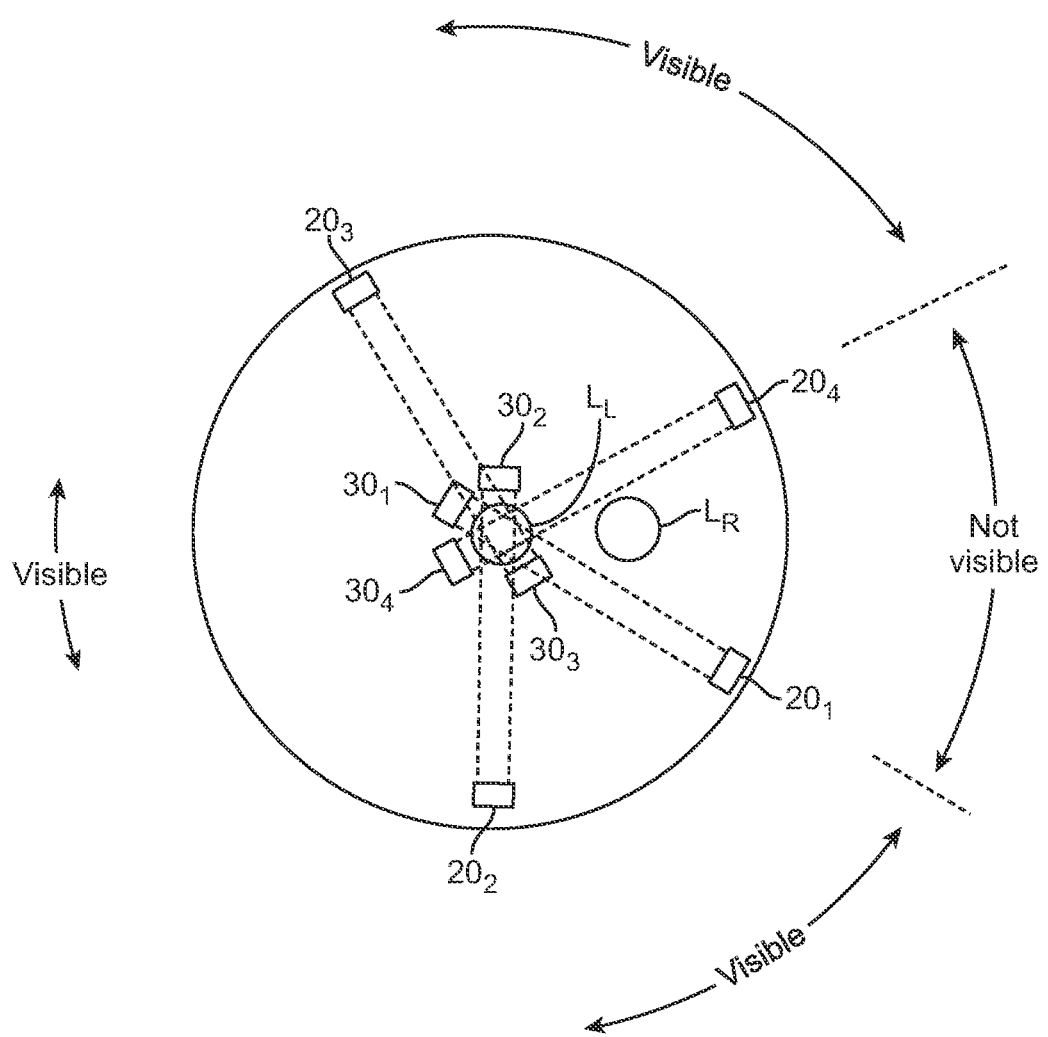
FIG. 7 is a top plan schematic showing the available scanning angles around a standing horse's left leg.

Further limitations of scanning a horse's leg can be realized by viewing FIG. 7 which shows the available scanning angles around a horse's left leg. Specifically, the horse's left leg $L_L$ and the horse's right leg $L_R$ are shown (as is the narrow separation distance between the legs). Four locations are shown where the scanner system would operate (and not be blocked by the horse's right leg $L_R$). Specifically, location $20_1/30_1$; location $20_2/30_2$; location $20_3/30_3$, and location $20_4/30_4$. As can be seen, it is only possible to scan about 270 degrees around the horse's leg. Specifically, it is not possible to scan with X-ray sources positioned in the arc of the circle between detector $20_1$ and $20_4$ (since right leg $L_R$ would shield left leg $L_L$ from view). Therefore, to improve the ability to scan around objects that that have limited clearances, the presently disclosed systems have additional embodiments that further increase the ability to scan in tight locations with limited clearances.

Figure 8:
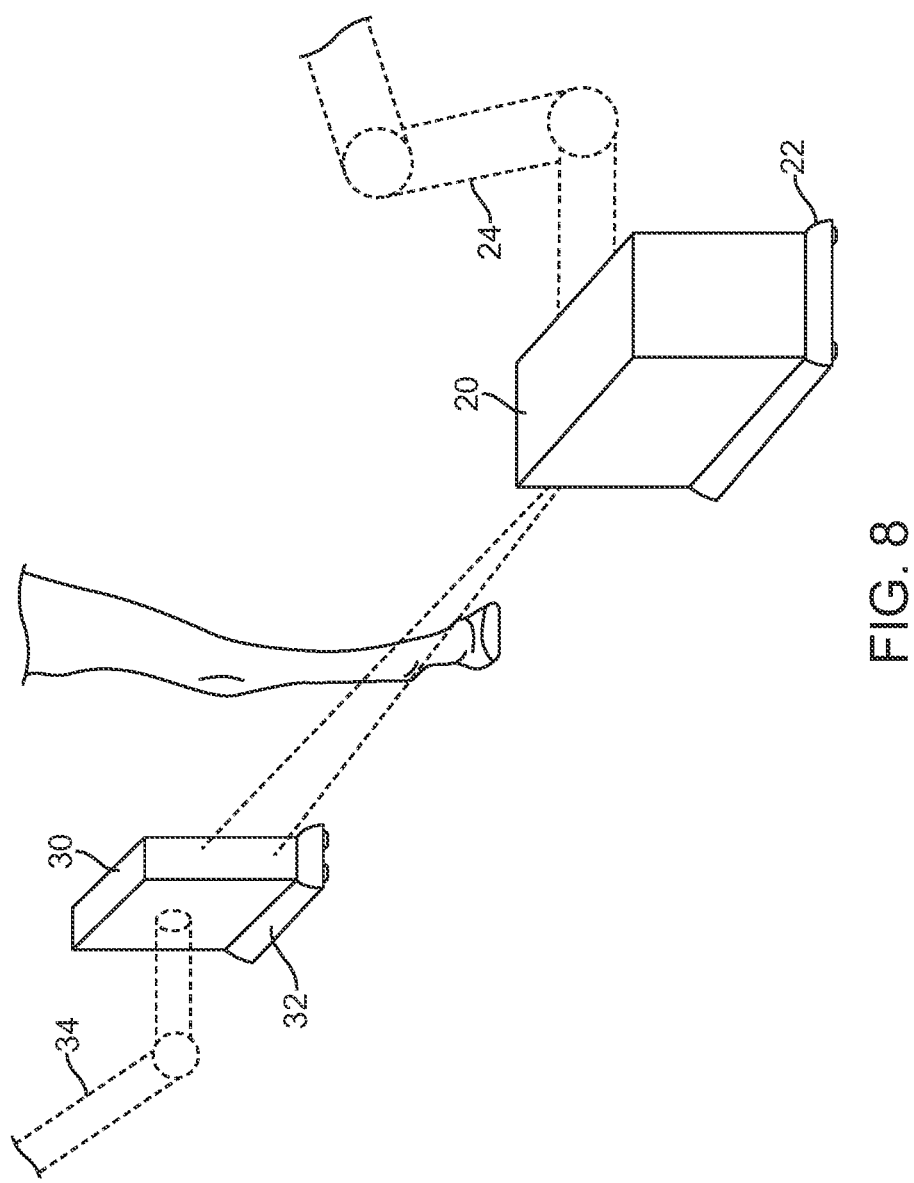
FIG. 8 is a perspective view of the scanning system of FIGS. 4 and 5, but using separate positioning systems for each of the linear array of X-ray sources and the linear X-ray detector.

For example, as seen in FIG. 8, each of X-ray sources 20 and X-ray detector 30 can be independently positionable (i.e.: they each have their own separate positioning system). It is to be understood, therefore, that the present system (as encompassed by the present claims) covers both "connected" positioning systems where both the X-ray sources 20 and X-ray detector 30 are moved together, and "independent" or "non-connected" positioning systems where each of X-ray sources 20 and X-ray detector 30 can be moved separately.

For example, X-ray sources 20 may be moveable on a positionable support cart, trolley, mechanical or robotic platform 22 that can be independently navigated across the floor and X-ray detector 30 may also be moveable on a positionable support cart, trolley, mechanical or robotic platform 32 that can be independently navigated across the floor. Alternatively, X-ray sources 20 may be moveable with a robotic arm 24 while X-ray detector 30 may be moveable with its own robotic arm 34. In addition, each of X-ray sources 20 and X-ray detector 30 may be hand-held or otherwise moved by an operator using any means or system whatsoever.

In addition, since the movement of the X-ray sources 20 and the movement of the X-ray detector 30 can be "decoupled" (i.e.: each can be moved independently), then the present system can also optionally be used for tomosynthesis data collection. Tomosynthesis involves limited angle tomography with a lower number of discrete exposures. This reduces the radiation exposure and operating costs. In addition, the use of approximation algorithms and digital processing allows a 3D image set to be reconstructed so that individual 2D planes of focus can be viewed through the 3D data set.

Figure 9:
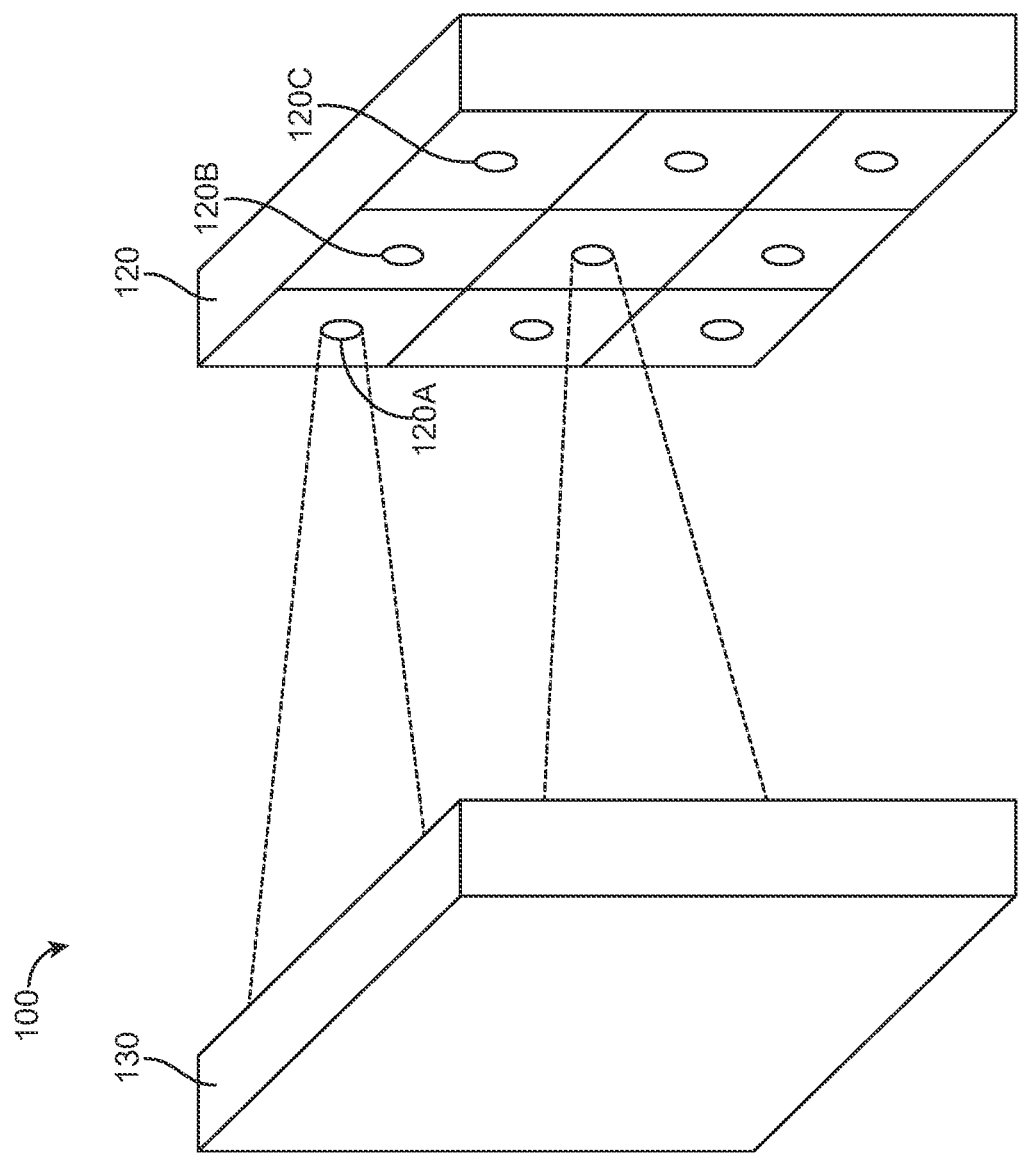
FIG. 9 is a perspective view of a scanning system having a 2D planar array of X-ray sources that emit cone-shaped beams and a planar X-ray detector viewed from a first angle.

FIG. 9 sets forth a Cone-Beam CT embodiment of the present system that optionally separates the movement of the X-ray sources 120 from the movement of X-ray detector 130, and also allows each of the X-ray sources 120 and X-ray detector 130 to independently rotate vertical axes passing through their centers. This, advantageously increase the angles through which the target (e.g. leg L) can be viewed, as follows.

Figure 10:
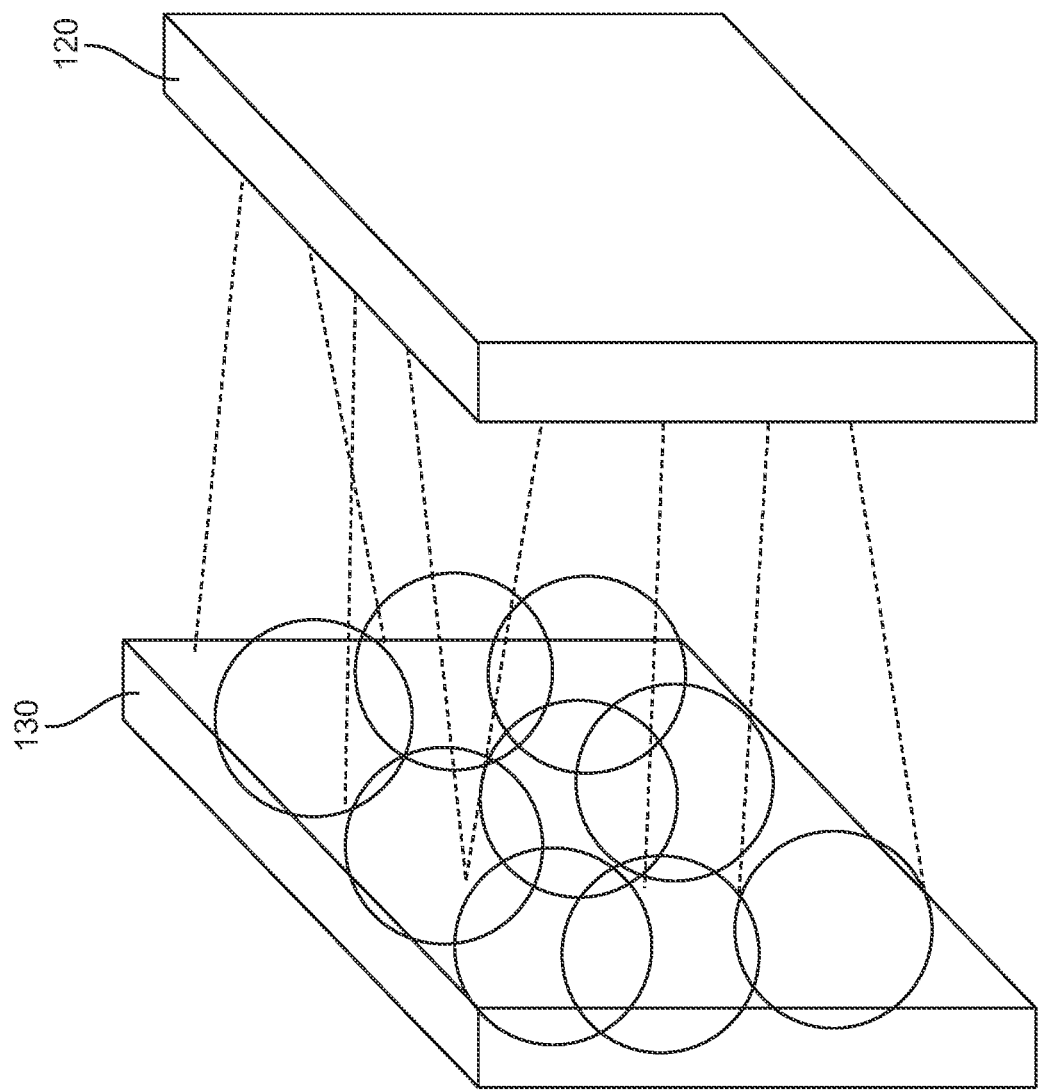
FIG. 10 is a perspective view of the scanning system of FIG. 9, viewed from a second angle.

FIGS. 9 and 10 show two different views of a scanning system 100 having a plurality of X-ray sources 120 (nine X-ray sources 120A, 12B, 120C, etc. arranged in a three by three planar array), and a planar X-ray detector 130. When the X-ray sources are arranged in a 3×3 array of these X-ray tubes, the array can have a size on the order of 10" wide by 12" high. Additionally, X-ray sources 20 may optionally be Toshiba X-ray tube DG-073B-DC or DG-073B-ACs which operate at 70 kV, 8 mA and have a 20 degree emission cone. An exemplary X-ray detector panel 130 can be the PaxScan® 4030CB manufactured by Varex Imaging Corporation. This detector has an active surface area of 15.6" by 11.6" and a maximum frame rate of 30 frames per second.

It is to be understood, however, that these dimensions and parts are merely exemplary and that any suitable parts and dimensions can be used, all keeping within the scope of the present system. The support housing for X-ray sources 120 is preferably small enough to contain all nine X-ray sources, the necessary wiring, cooling means and shielding.

An advantage of using nine separate X-ray emitters 120 is that the duty cycle of each X-ray emitter is only $\frac{1}{9}^{th}$ what would be required in the case of a single emitter. This advantageously reduces the heat loading on each of the emitters, and reduces the heat capacity for each emitter. The reduction in the source-to-detector distance also reduces the overall system power requirements.

Figure 11:
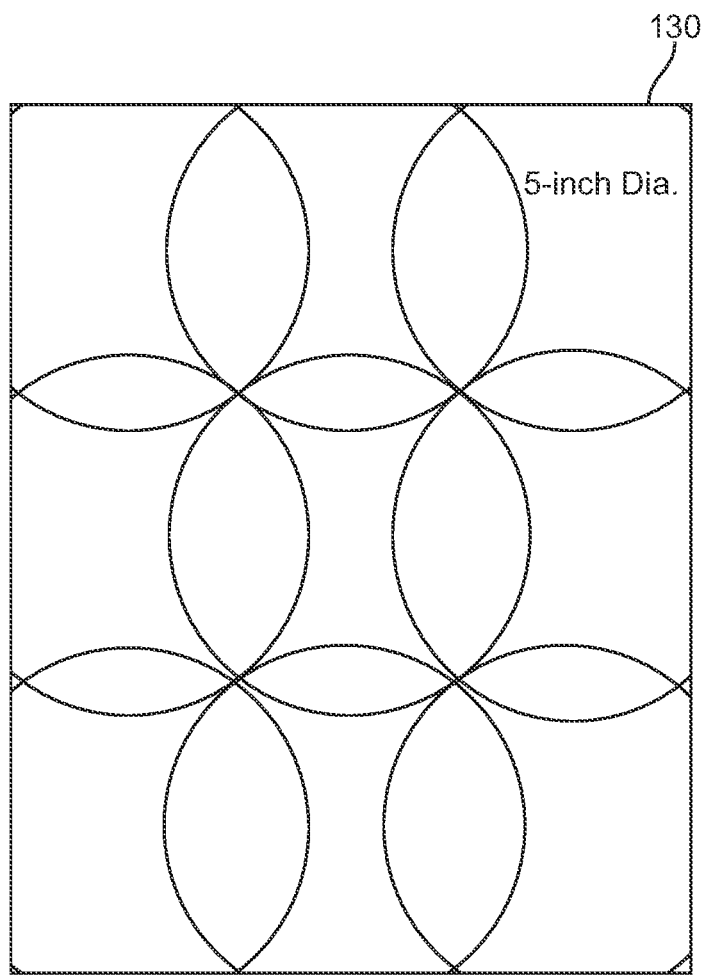
FIG. 11 is a front elevation view of the planar detector showing an overlap of C-shaped X-ray beams on the proximal (i.e.: source-facing) side of the target.
Figure 12:
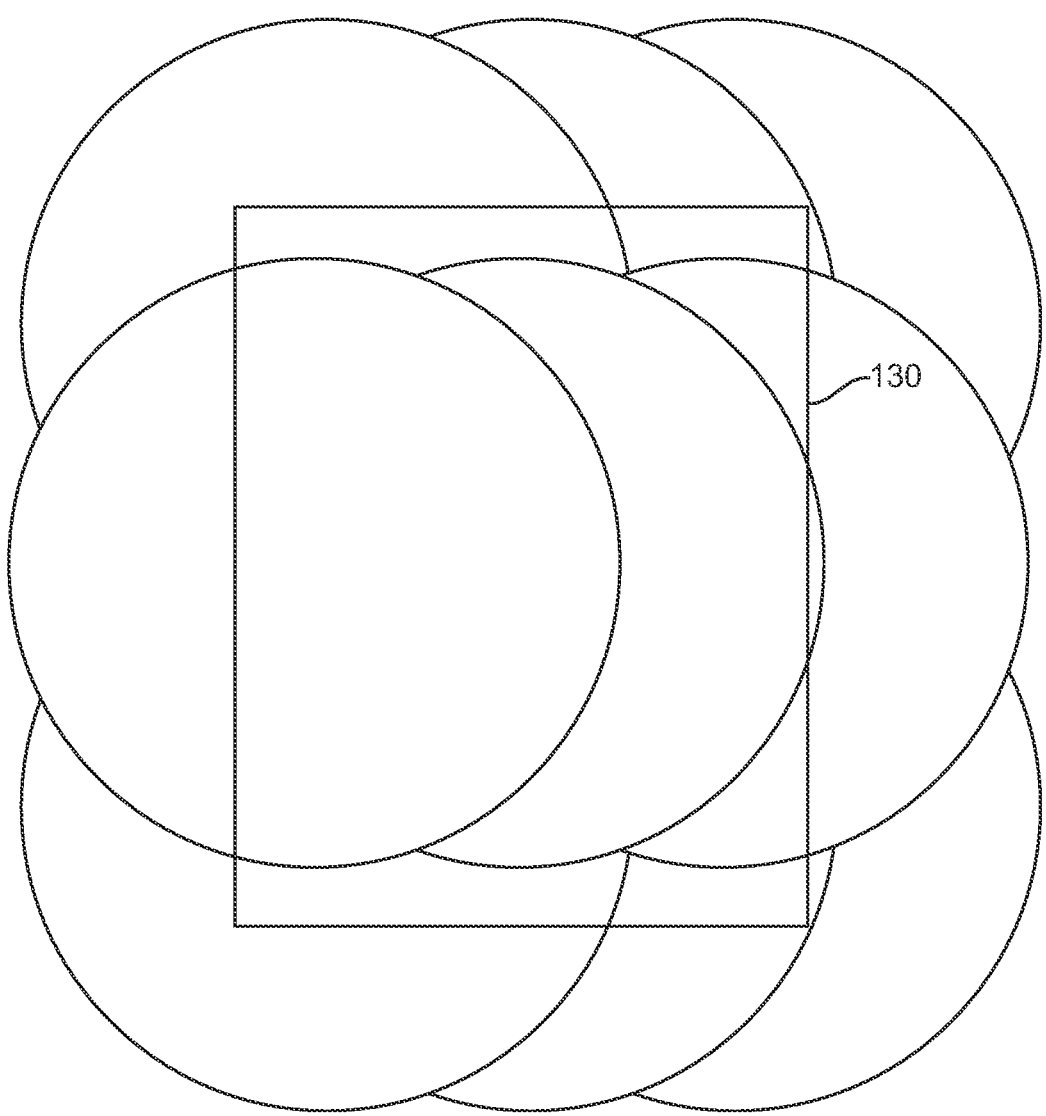
FIG. 12 is another front elevation view of the planar detector showing an overlap of C-shaped X-ray beams on the distal (i.e.: detector facing) side of the target.

In the cone-shaped beam embodiment of FIGS. 9 and 10, the cone-shaped beams overlap (as shown in FIGS. 11 and 12) to completely fill detector array 130. Such an overlap of the cone-shaped beams provides an improved image quality. Moreover, using nine X-ray sources 120 provides more image data than simply stacking three X-ray sources one above another. This is because the two side columns of X-ray sources will pass through the sides of the leg, which adds additional data for image reconstruction.

Using a two dimensional array of X-ray sources 120 and a planar X-ray detector 130 having overlapping cone-shaped beams on the X-ray detector 130 has the advantage of ensuring that the proximal side of the target being imaged is exposed to sufficient X-rays, thereby reducing the need for additional scans and/or increasing the X-ray source to detector distance.

Unfortunately, although cone-shaped beam systems have advantages over fan-shaped beam systems, it is still difficult to fit a comparatively large detector 130 between a horse's legs (due to the width of the detector itself. To overcome this problem, the present system includes additional aspects in which positioning systems are provided to ease the detector 130 between the horse's legs without interrupting the scanning procedure.

Figure 13:
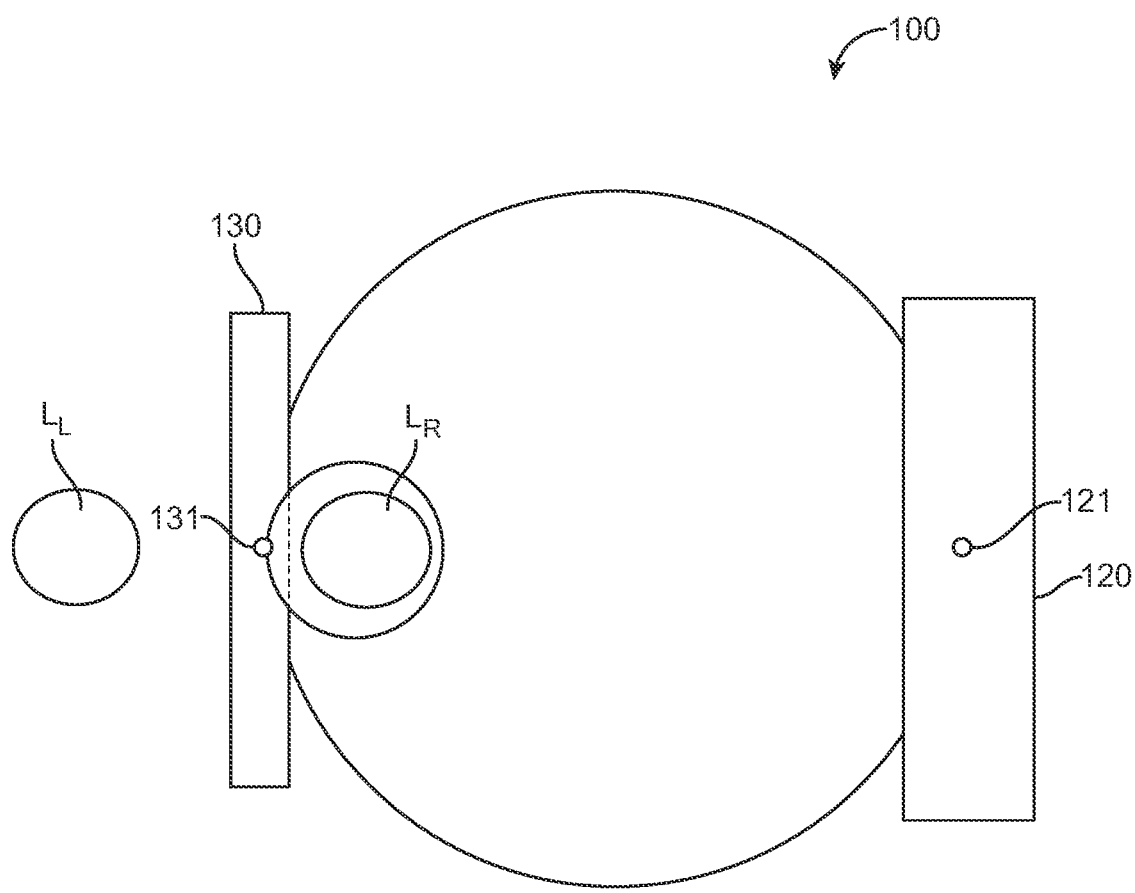
FIG. 13 is a top plan view of the scanning system of FIGS. 9 and 10 illustrating the positioning of the scanning system around a horse's right leg.

Specifically, FIG. 13 shows a system for scanning the right leg $L_R$ of a horse (in which planar detector 130 is positioned between the legs such that the scan may be completely performed around the full circumference of the leg. Specifically, FIG. 13 shows the mid-way position of the scan with X-ray source 120 and X-ray detector positioned are parallel to one another (such that their opposing faces are perpendicular to one another).

A preferred method of movement of the X-ray source and the X-ray detector will also be explained below in relation to FIGS. 23A to 23J. It is to be understood, however, that movement that aligns the X-ray sources with the X-ray detector (while the detector moves between the horse's legs) can also be achieved with system 100 by moving X-ray source 120 around its central vertical axis 121 and by moving X-ray detector 130 around its central vertical axis 131. These rotational movements are done at the same time that X-ray source 120 and X-ray detector 130 are rotated around the horse's leg. In optional embodiments, X-ray detector 130 is 15" tall and 12" wide. In contrast, traditional flat-panel detectors are from 14" to 17" wide.

Figure 14:
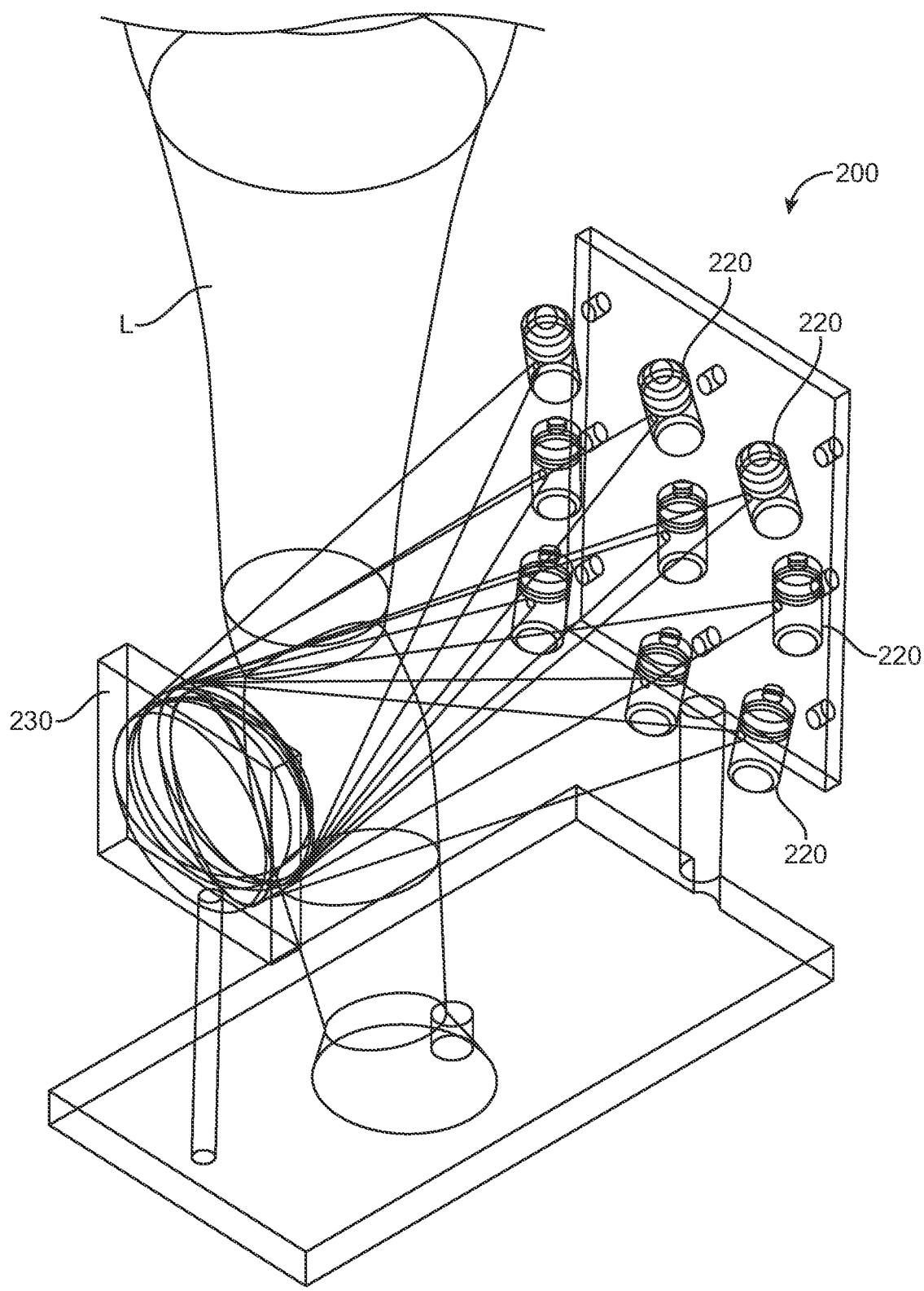
FIG. 14 is a perspective view of a spherical placement of X-ray sources incident on a single planar X-ray detector.
Figure 15:
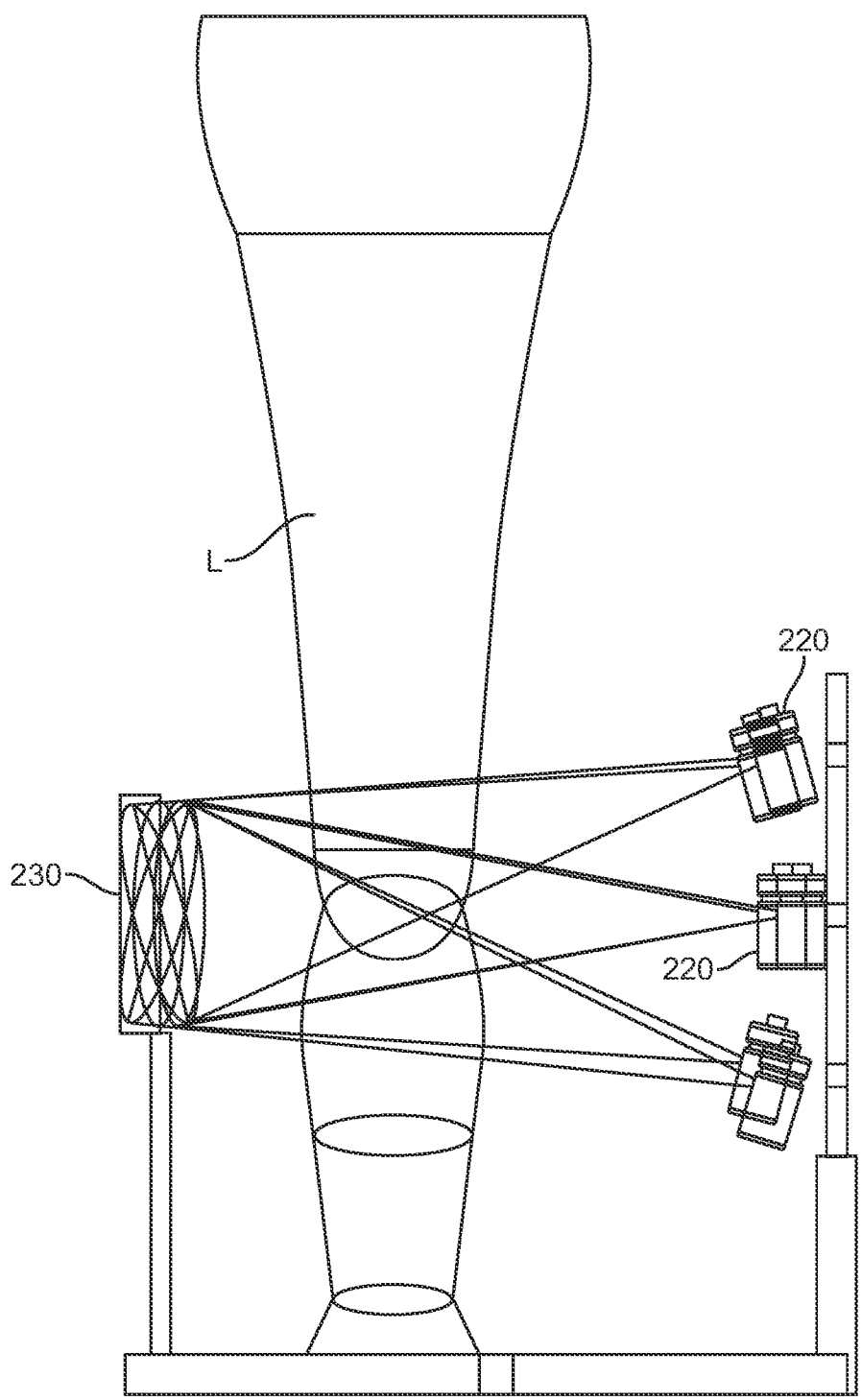
FIG. 15 is a side elevation view corresponding to FIG. 14.
Figure 16:
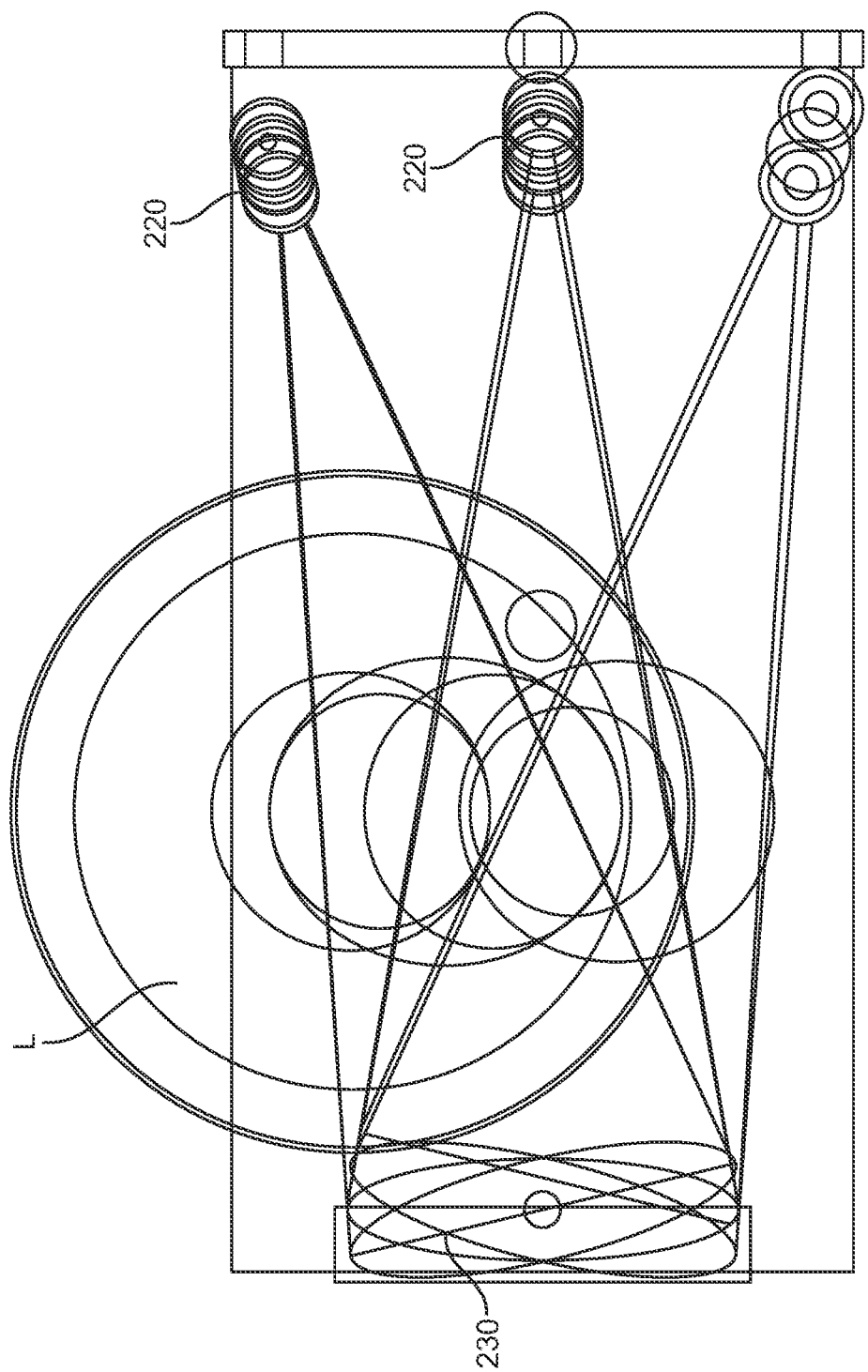
FIG. 16 is a top plan view corresponding to FIGS. 14 and 15.

FIGS. 14 to 16 show a spherical placement of X-ray sources incident on a single planar X-ray detector. Specifically, system 200 includes a plurality of X-ray sources 220 arranged generally equidistantly from X-ray detector 230. Preferably, X-ray sources 220 and detector 230 are both rotated around the leg L (similar to systems 10 and 100). The advantage of this arrangement is that it allows a hi-resolution focus on the joints of the leg. Specifically, more of the beams are passing through a smaller portion of tissue, thereby enabling more detailed imaging of that region of tissue.

Figure 17:
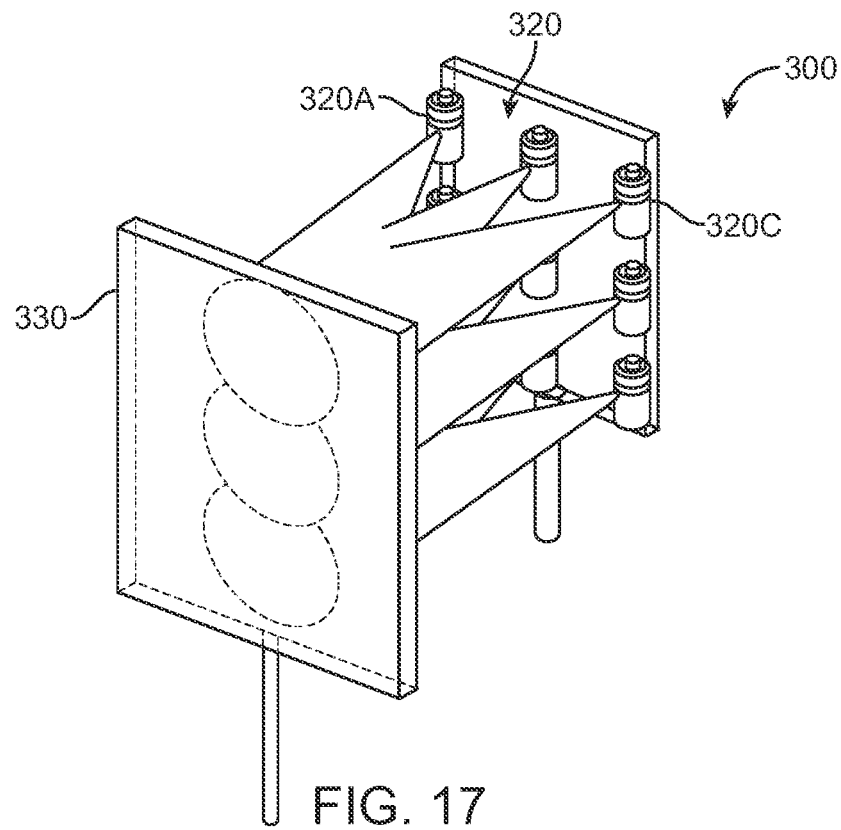
FIG. 17 is a perspective view of another embodiment of a planar placement of X-ray sources incident on a single planar X-ray detector.
Figure 18:
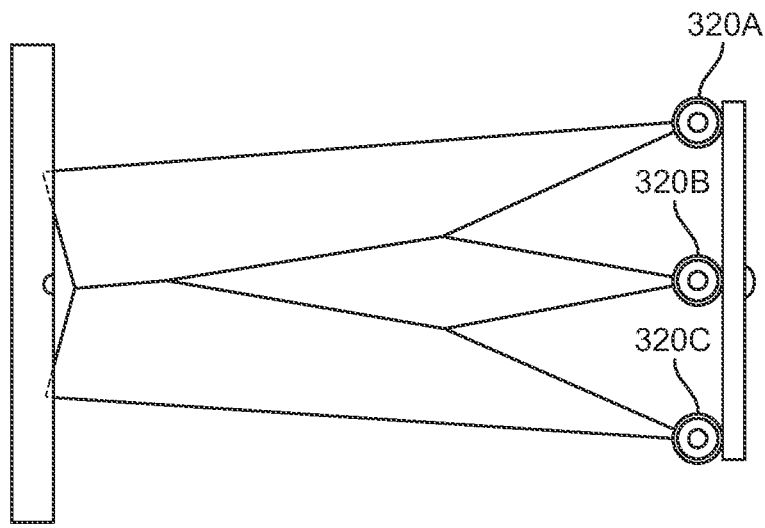
FIG. 18 is a top plan view corresponding to FIG. 17.
Figure 19:
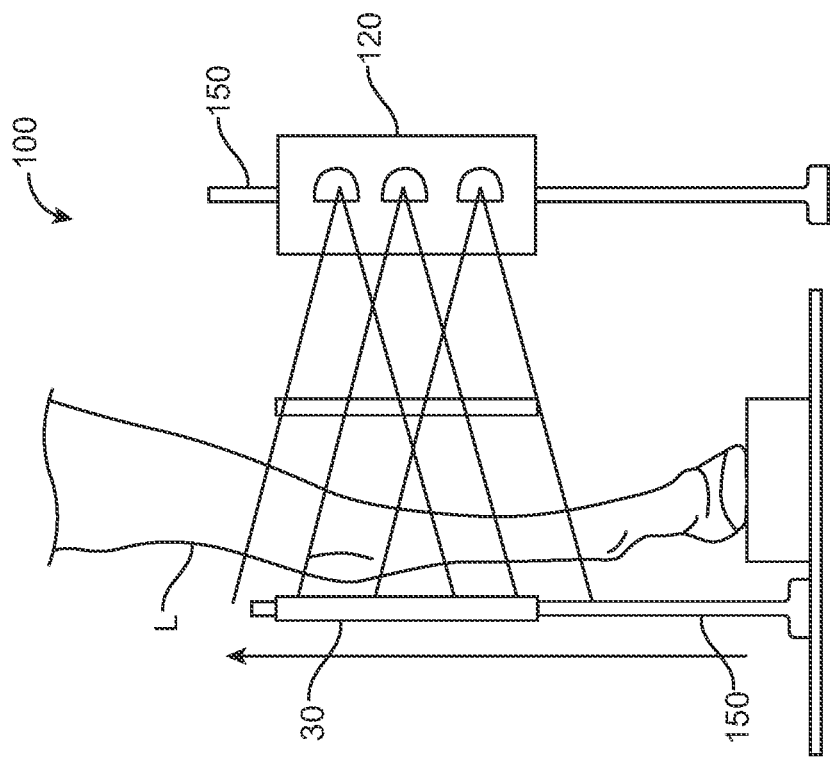
FIGS. 19 and 20 show positioning systems that provide for vertical movement of a planar array of X-ray sources and an X-ray detector.
Figure 20:
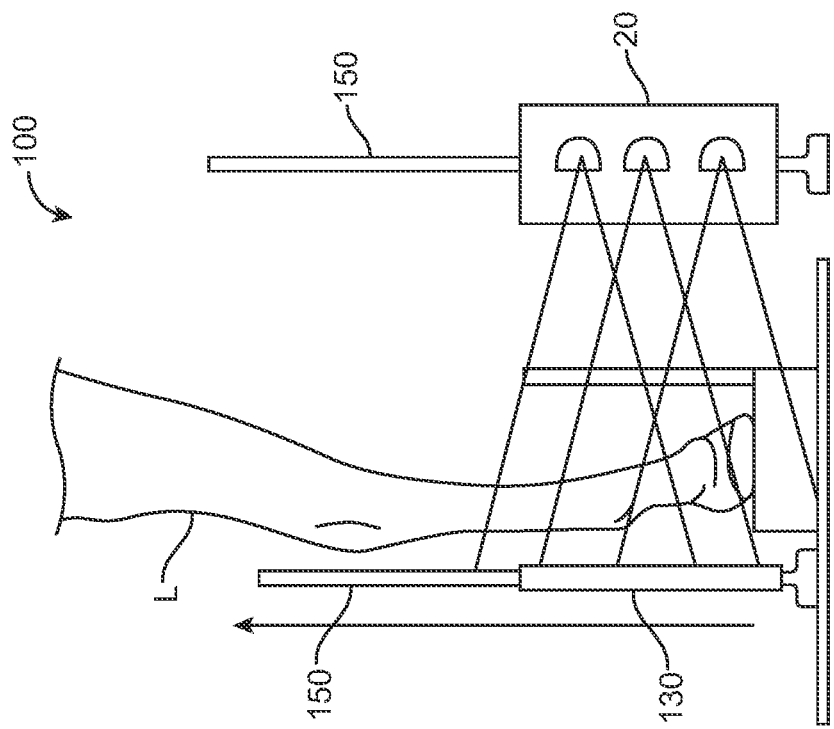
Figure 22:
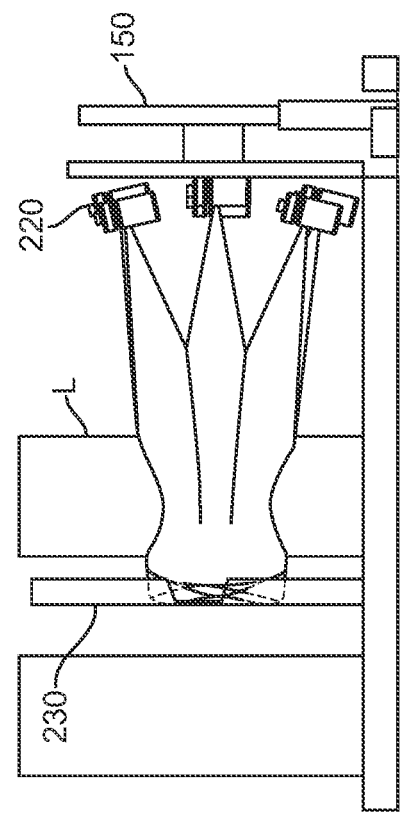
FIGS. 21 and 22 show positioning systems that provide for vertical movement of a planar array of X-ray sources and an X-ray detector.
Figure 21:
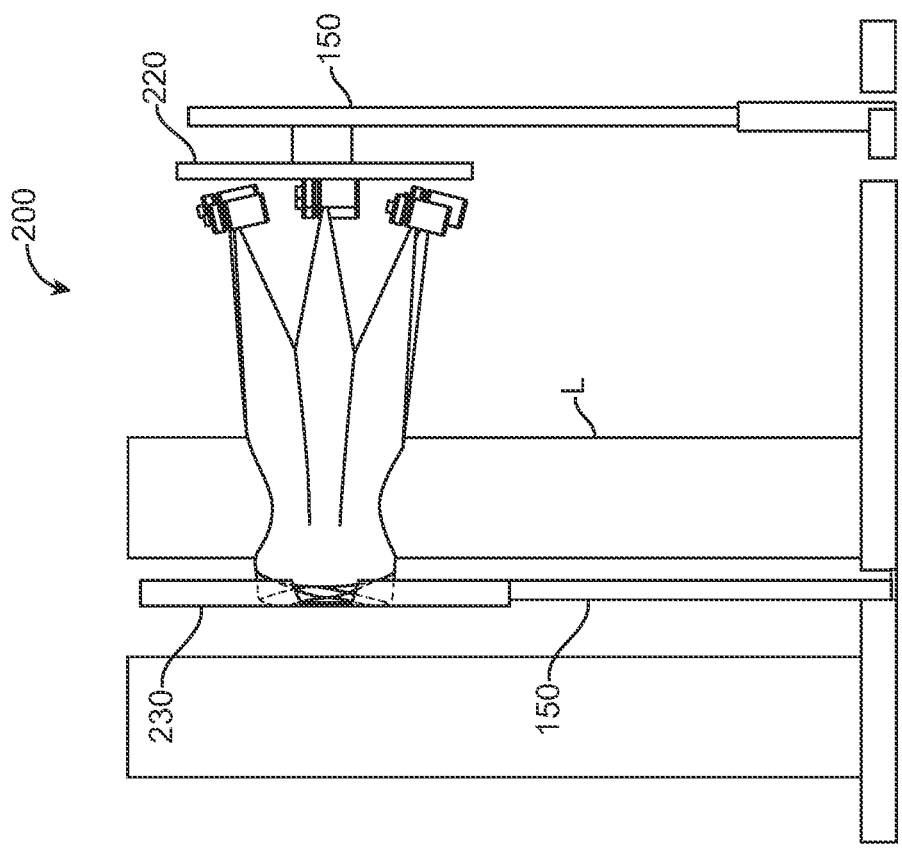

FIGS. 17 and 18 illustrate a scanning system 300 having a plurality of X-ray sources 320 (nine X-ray sources arranged in a three by three planar array), and a planar X-ray detector 330. In this embodiment, the top row of three sources (320A, 320B and 320C) all have beams that substantially fully overlap near the top of X-ray detector 330. Similarly, the middle row of three sources all have beams that overlap. Below this, the bottom three sources all have beams that overlap below on X-ray detector 330. It is to be understood that in one version of this embodiment, the individual sources are all disposed on a planar array. However, in another version of this embodiment, the individual sources can be disposed in a cylindrical format (i.e.: with the three columns of sources each being equidistant from a vertical axis passing through the target tissue). Should the X-ray sources instead be positioned in a cylindrical arrangement (as opposed to spherical), this advantageously makes the image reconstruction algorithms easier.

Next, FIGS. 19 to 22 show an optional system for simultaneously raising and lowering X-ray sources 20 and X-ray detector 30 (or X-ray sources 120 or 220 and X-ray detector 130 or 230). Specifically, in FIGS. 19 and 21, X-ray sources 20 or 220 and X-ray detector 30 or 230 are seen in their lowered position and in FIGS. 20 and 22, X-ray sources 20 or 220 and X-ray detector 30 or 230 are seen in their raised position. This is accomplished by a longitudinal positioning system 150 which may comprise any mechanical device or system for raising and lowering X-ray sources 20 or 220 and X-ray detector 30 or 230.

The advantage of longitudinal positioning system 150 is that the full length of leg L can be imaged by a scanner having X-ray sources 120 and X-ray detector 130 that are much shorter than the full length of the leg to be imaged. It is advantageous to acquire CT images of the lower 27 inches of the horse's leg as this ensures that the carpal, fetlock, pastern and coffin joints (of the front legs) and the hock and fetlock joints (of the rear legs) are all imaged. When using a 12 inch high X-ray detector 30, it is therefore desirable to move the detector and X-ray sources up and down along the vertical height of the leg. For other extremity CT applications such as the human head, it is not necessary to provide eccentric source and detector rotation axes. Rather, both the X-ray sources and the detector can be rotated around the target.

It is to be understood that a longitudinal positioning system 150 becomes less needed when the X-ray sources 20 or 120 or 220 or 320 and X-ray detector 30 or 130 or 230 or 330 are taller, and more important when the X-ray sources and X-ray detector are shorter. In fact, simply making a sufficiently tall system 10 or 100 or 200 or 300 may avoid the need for a longitudinal positioning system 150 completely.

It is also to be understood that although longitudinal positioning system 150 is illustrated as providing vertical movement, the present system encompasses and longitudinal movement along the length of an elongated member (such as a limb, arm, or other object). Such movement may be vertical, horizontal movement in or any other angle.

Lastly, FIGS. 23A to 23J illustrate a preferred system of sequential movement of the present scanning system components around the leg of a horse. As can be seen, the X-ray sources 120 and X-ray detector 130 remain parallel to one another as they are both advanced around the leg. It is to be understood that although FIGS. 23A to 23J illustrate this movement in the context of system 200, this preferred movement could also be achieved by systems 10, 100, or 300, as desired. The method illustrated in FIG. 23 is designed to move detector 330 between the horse's legs while still keeping the source 320 facing the detector 330. In addition, this preferred method allows detector 330 to rotate in a much smaller radius around leg L than source 220 rotates in.

First, in FIG. 23A, detector 230 is positioned behind the horse's left leg $L_L$ and is not blocked by the horse's right leg $L_r$. In FIG. 23B, both the detector 230 and source 220 are rotated around the left leg. Next, in FIG. 23C, detector 220 is moved slightly to one side of the incoming beams (such that the X-ray beams are directed more to one side of the detector 230 than the other, as shown). FIG. 23D continues this rotation of detector 230 and sources 220. Next, in FIG. 23E, detector 230 is moved forward (i.e.: translated laterally) between the horse's legs (such that the beams again target the center of detector 230). FIG. 23F shows the continuing forward movement of detector 330 between the horse's legs. As can be seen, the beams now are more directed to the other side of the detector 230. In FIG. 23G, both the sources 220 and detector 230 again begin to rotate about the left leg. This rotation continues through the positions illustrated in FIGS. 23H, 23I, and 23J. During this period of time, the beams can be re-centered on detector 230 (by moving detector 230 with respect to sources 220). Thus, the positioning system for rotating X-ray detector 230 can optionally both rotate the X-ray detector around the target and also translate the X-ray detector laterally with respect to the beams emitted by the X-ray sources.

Although FIGS. 23A to 23J illustrate a lateral movement of detector 230 with respect to sources 220 as a method of moving the detector between the horse's legs, it is to be understood that another approach is to rotate each of the sources and detectors about central vertical axes passing therethrough. For example, referring back to FIG. 13, X-ray source 120 can be rotated about its central vertical axis 121 and X-ray detector 130 can be rotated about its central vertical axis 131 as the source 120 and detector 130 are each rotated around the horse's leg. Additionally, it is to be understood that any combination of rotational and translational movement of the X-ray source and X-ray detector with respect to one another (to move the X-ray detector between the horse's legs) is encompassed within the scope of the present system.

What is claimed is:

1. A scanning system, comprising:
    an X-ray detector;
    a plurality of X-ray sources positioned in a spherical orientation with respect to the X-ray detector;
    a positioning system for rotating the X-ray detector in a first radius around the target; and
    a positioning system for rotating the plurality of X-ray sources in a second radius around the target;
    wherein the first radius is smaller than the second radius.

2. The scanning system of claim 1, wherein the plurality of X-ray sources are mounted on a single moveable support.

3. The scanning system of claim 1, wherein the positioning system for rotating the X-ray detector and the positioning system for rotating the plurality of X-ray sources are connected together to simultaneously rotate the X-ray detector and the plurality of X-ray sources around the target.

4. The scanning system of claim 1, wherein the positioning system for rotating the X-ray detector and the positioning system for rotating the plurality of X-ray sources are not connected together such that the X-ray detector and the plurality of X-ray sources can be moved independently of one another.

5. The scanning system of claim 1, wherein the X-ray detector is a linear detector, and each of the X-ray sources emit a fan-shaped beam.

6. The scanning system of claim 5, wherein the fan-shaped beams are aligned with the length of the linear X-ray detector such that edges of the fan-shaped beams overlap one another long the length of the linear detector.

7. The scanning system of claim 1, further comprising:
a control system for sequentially activating the X-ray sources.

8. The scanning system of claim 7, wherein the control system activates different X-ray sources at the same time, but wherein adjacent X-ray sources are not activated at the same time.

9. The scanning system of claim 1, further comprising:
a longitudinal positioning system for simultaneously moving the X-ray sources and the X-ray detector longitudinally along the length of the target.

10. The scanning system of claim 9, wherein the longitudinal positioning system simultaneously moves the X-ray sources and the X-ray detector vertically up and down.

11. The scanning system of claim 1, wherein X-ray beams from each of the X-ray sources are cone-shaped beams that fully overlap one another on the X-ray detector.

12. The scanning system of claim 1, wherein the target is an extremity of an animal.

13. The scanning system of claim 12, wherein the extremity of an animal is a horse's leg.

14. A scanning system comprising:
a plurality of X-ray sources that each emits a cone-shaped beam;
an X-ray detector that is a planar detector;
a positioning system for rotating the X-ray detector in a first radius around the target; and
a positioning system for rotating the plurality of X-ray sources in a second radius around the target, the first radius being smaller than the second radius;
wherein the positioning system for rotating the X-ray detector both rotates the X-ray detector around the target, and rotates the X-ray detector about an axis, and
wherein the positioning system for rotating the X-ray sources both rotates the X-ray sources around the target, and rotates the X-ray sources about an axis.

15. The scanning system of claim 14, wherein the edges of the cone-shaped beams overlap one another across the surface of the planar detector.

16. The scanning system of claim 14, wherein the axis about which the X-ray detector rotates passes through the X-ray detector, and the axis about which the X-ray sources rotate passes through the X-ray sources.

17. The system of claim 14, wherein the positioning systems keep the X-ray sources parallel to the X-ray detector as both the X-ray sources and X-ray detector are rotated around the target.

18. The scanning system of claim 14, wherein the positioning system for rotating the X-ray detector both rotates the X-ray detector around the target, and translates the X-ray detector laterally with respect to the beams emitted by the X-ray sources.

19. The scanning system of claim 14, wherein the plurality of X-ray sources comprise 9 X-ray sources arranged in a 3×3 array.

20. A method of scanning a target, comprising:
providing a plurality of X-ray sources on a first support;
providing an X-ray detector on a second support; and
imaging a target by rotating the plurality of X-ray sources around an axis and rotating the X-ray detector around another axis while simultaneously rotating the plurality of X-ray sources and the X-ray detector around the target, while
sequentially emitting overlapping beams from the plurality of X-ray sources onto the X-ray detector.

21. The method of claim 20, wherein the X-ray detector is rotated in a smaller radius around the target than the plurality of X-ray sources are rotated around the target.

22. The method of claim 20, wherein the X-ray detector and the X-ray sources are connected together to simultaneously rotate around the target.

23. The method of claim 20, wherein the X-ray detector and the plurality of X-ray sources are not connected together such that the X-ray detector and the plurality of X-ray sources can be moved independently of one another around the target.

24. The method of claim 20, wherein the overlapping beams are fan-shaped beams.

25. The method of claim 20, wherein the overlapping beams are cone-shaped beams.

26. The method of claim 20, wherein the plurality of X-ray sources are rotated around an axis passing therethrough, and the X-ray detector is rotated around an axis passing therethrough.

27. The method of claim 26, further comprising:
rotating both the X-ray detector and the plurality of X-ray sources such that the plurality of X-ray sources and X-ray detector remain parallel to one another when rotated around the target.

28. The method of claim 20, wherein sequentially emitting overlapping beams comprises activating different X-ray sources at the same time, but not activating adjacent X-ray sources at the same time.

29. The method of claim 20, further comprising:
simultaneously moving the X-ray sources and the X-ray detector longitudinally along the length of the target.

30. The method of claim 20, wherein the X-ray sources are positioned in a spherical or cylindrical orientation with respect to the X-ray detector, and each of the X-ray sources emit a cone-shaped beam.

31. The method of claim 20, wherein the target is an extremity of an animal.

* * * * *